United States Patent [19]

Kazmiroski et al.

[11] 4,384,003

[45] May 17, 1983

[54] CONTRACEPTIVE SUPPOSITORY

[75] Inventors: Michael S. Kazmiroski, Philadelphia; Wilmer E. Latshaw, Berwyn, both of Pa.

[73] Assignee: Menley & James Laboratories, Ltd., Philadelphia, Pa.

[21] Appl. No.: 278,040

[22] Filed: Jun. 29, 1981

[51] Int. Cl.³ .............................................. A61K 31/09
[52] U.S. Cl. ..................................... 424/341; 424/361; 424/DIG. 15; 424/DIG. 14
[58] Field of Search ............... 424/341, 361, DIG. 14, 424/DIG. 15

[56] References Cited

U.S. PATENT DOCUMENTS 4,187,286 2/1980 Marcus ................................. 424/44

OTHER PUBLICATIONS

Lachman et al., "The Theory and Practice of Industrial Pharmacy", 2nd Ed., 1976, pp. 256-260.
Edward Mendell Co., *Inc. Bulletin*, "Explotab".
Kirk-Othmer, Encyclopedia of Chem. Tech., 2nd Ed., vol. 4, pp. 594-595, (1964).

*Primary Examiner*—Leonard Schenkman
*Attorney, Agent, or Firm*—Joseph A. Marlino; Richard D. Foggio; Alan D. Lourie

[57] ABSTRACT

A vaginal contraceptive suppository having both a rapid release of active ingredient and prolonged duration of effectiveness. The suppository comprises a mixture of sodium starch glycolate, a thickening agent and a vegetable oil base combined with a spermicide.

4 Claims, No Drawings

CONTRACEPTIVE SUPPOSITORY

This invention relates to contraceptive suppositories adopted for vaginal insertion.

Prior to this invention commercial contraceptive suppositories were usually preferred with a water soluble base, such as polyethylene glycol, which dissolves quite rapidly when inserted in the vaginal cavity and releases the spermicide ingredient. Although fast acting, approximately fifteen minutes, these commercial suppositories have two major disadvantages. First, they dissolve in the aqueous media of the vaginal cavity to form thin, runny solutions that are messy and tend to leak rapidly from the cavity. Second, they remain effective for only a short period of time, no more than an hour.

Attempts have been made to solve the above problems by using other suppository bases. For example, oil soluble glycerides of natural fatty acids (synthetic butters) which are widely used in rectal suppositories have been considered. These vehicles melt at body temperature to release their active ingredient and are somewhat more viscous than the water soluble bases. However, the release of the active ingredient from such vehicles is delayed. In vitro sperm immobilization tests show that up to two hours is required to obtain effective levels of spermicidal action. This is an undesirable delay for such products because commercial products state on the label that they should be used ten to fifteen minutes prior to intercourse and are effective for only one hour.

It is therefore an object of this invention to provide a vaginal contraceptive suppository which has rapid spermicidal action and also a long duration of spermicidal effectiveness. It is a further object of this invention to provide a suppository which prevents leaking from the vaginal cavity and therefore keeps the active ingredient in place to permit prolonged duration of effectiveness.

The novel suppositories of this invention comprise a mixture of a thickening agent, a wicking agent such as sodium starch glycolate, and a spermicide in a base comprised of oil soluble glycerides of natural fatty acids.

It has been discovered that these ingredients must be present in combination in order to achieve the advantages noted above. If the oil soluble base is employed alone, the release of the active ingredient is delayed. At least two hours is required to obtain effective levels of spermicidal action. When the wicking agent is added, release of the active ingredient is much faster, decreasing from two hours to fifteen minutes. However, although providing rapid release of the active ingredient, the suppository is still unsatisfactory because upon melting it tends to run and leak from the vaginal orifice. Thus the effective duration of spermicidal effectiveness is less than desired.

To overcome this problem, it was discovered that the addition of the third essential ingredient, a thickening agent, to the oil vehicle will hydrate as the suppository melts in the aqueous environment of the vaginal cavity to produce a thick, non-runny paste which will not leak from the orifice and thus provide an effective spermicidal action for a longer period of time.

The thickening agent, preferably methylcellulose, will be present from about 3% to about 10% by weight. Most advantageously, the thickening agent will be present from about 5% to about 8% by weight. Other substances which may be employed as thickening agents are water hydrating gums such as carboxymethylcellulose, hydroxypropylcellulose, guar gum or sodium alginate.

The wicking agent will be present from about 10% to about 40%; preferably from about 15% to about 25%. Most advantageously, sodium starch glycolate sold under the tradename of "Explotab" is employed as the wicking agent.

The oil soluble suppository base may be any of the synthetic butter compounds such as, for example, cocoa butter. Preferably the base is a hard butter which is a specially processed vegetable fat made from partially hydrogenated palm kernel oil sold under the tradename of "SP-8".

The vaginal contraceptive suppository according to this invention contains additionally a spermicidally active ingredient. Most advantageously, the spermicide is nonoxynol-9, nonylphenoxypolyethoxy ethanol or octoxynol-9, octylphenoxypolyethoxyethanol. The spermicide is present from about 3.0% to about 7.0% by weight or from about 50 mg. to about 100 mg. per suppository.

When necessary, any desired pharmaceutically compatible adjuvant used in the preparation of suppositories by those skilled in the art may be employed. For example, preservatives such as methylparaben, propylparaben or sorbic acid can optionally be included in the preparation.

The invention will be further clarified by the following specific example. This example is not limiting but is used to make obvious to one skilled in the art the full practice of the method of the invention.

EXAMPLE

| Ingredients | % W/W | Mg./1.60 Gram Suppository |
|---|---|---|
| Sodium Starch Glycolate ("Explotab") | 25.0 | 400.0 |
| Methylcellulose, USP | 7.5 | 120.0 |
| Sorbic Acid, N.F. | 0.1 | 1.6 |
| Nonoxynol-9 | 6.4 | 102.4 |
| SP-8 Hard Butter | 61.0 | 976.0 |

In a steam bath the SP-8 hard butter was melted with mixing. The melted butter was placed into a jacketed Ross Mixer with a bowl temperature setting of 50° C. and mixed at 40 R.P.M. The nonoxynol-9 was then added to the butter with continued mixing.

The "Explotab", methylcellulose and sorbic acid were separately mixed and this mixture was slowly added to the butter while maintaining a bowl temperature of 50° C. and mixing at 40 R.P.M. for approximately thirty minutes.

The mixture was then poured into appropriate molds and cooled to 15° C.

Human in vivo comparative studies have been conducted with commercial suppositories and the vaginal contraceptive suppository of this invention. The method employed was as follows. A suppository was inserted at time zero. After five minutes, the subject engages in artificial intercourse with live sperm being injected into the vagina. Vaginal fluid samples are then withdrawn from three different vaginal areas and tested for live sperm. This test procedure was repeated at additional time intervals of fifteen minutes, one hour, two hours, four hours, six hours, and eight hours.

These in vivo tests demonstrated that the vaginal suppository of this invention released the active ingredient at effective spermicidal levels in less than fifteen minutes and that it had a duration of effectiveness up to six hours. This was in contrast to the commercial suppositories which lost their effectiveness in one hour.

What is claimed is:

1. A vaginal contraceptive suppository having both a rapid release and prolonged duration of effectiveness of active ingredient, comprising from about 3% to about 10% of a thickening agent, from about 10% to about 40% of sodium starch glycolate, from about 3% to about 7% of a spermicide and a suppository base comprising oil soluble glycerides of natural fatty acids.

2. The suppository according to claim 1 wherein the thickening agent is methylcellulose.

3. The suppository of claim 2 wherein the spermicide is nonoxynol-9.

4. The suppository of claim 1 wherein the thickening agent is present from about 5 to about 8 percent, the sodium starch glycolate from about 15 to about 25 percent, and the spermicide from about 3.0 to about 7.0 percent.

* * * * *